US00PP23712P2

(12) United States Plant Patent
Osiecki

(10) Patent No.: US PP23,712 P2
(45) Date of Patent: Jul. 2, 2013

(54) ***SPATHIPHYLLUM* PLANT NAMED 'S39'**

(50) Latin Name: ***Spathiphyllum* hybrid**
Varietal Denomination: S39

(75) Inventor: Marian Osiecki, Marianna, FL (US)

(73) Assignee: Oglesby Plants International, Altha, FL (US)

( * ) Notice: Subject to any disclaimer, the term of this patent is extended or adjusted under 35 U.S.C. 154(b) by 0 days.

(21) Appl. No.: 13/200,513

(22) Filed: Sep. 23, 2011

(51) Int. Cl.
*A01H 5/00* (2006.01)

(52) U.S. Cl.
USPC ..... Plt./364

(58) Field of Classification Search
USPC ..... Plt./364
See application file for complete search history.

*Primary Examiner* — Susan McCormick Ewoldt
(74) *Attorney, Agent, or Firm* — Cassandra Bright

(57) ABSTRACT

A new and distinct *Spathiphyllum* cultivar named 'S39' is disclosed, characterized by dark green, glossy foliage, early foliage production and rapid, compact growth. The new variety maintains its dark green foliage color under higher than normal light conditions, or low nutrient levels. The new variety is commercially suitable for six inch pot production. The new variety is a *Spathiphyllum*, typically produced as an indoor ornamental plant.

1 Drawing Sheet

Latin name of the genus and species: *Spathiphyllum* hybrid.

Variety denomination: 'S39'.

BACKGROUND OF THE INVENTION

The new cultivar is a product of a planned breeding program. The objective of the breeding program was to develop new *Spathiphyllum* varieties suitable for 6 inch commercial pot production, and with fast growth, and dark green foliage. The new variety originated from a cross pollination of a proprietary, unpatented seed parent referred to as '03-3-1' and the pollen parent, 'Power Petite' U.S. Plant Pat. No. 15,649. The crossing was made during April 2005.

The new variety was discovered by the inventor, Marian Osiecki, a citizen of the US, in September 2006 in a group of seedlings resulting from the crossing. The new cultivar was found in a commercial greenhouse in Altha, Fla.

Asexual reproduction of the new cultivar 'S39' was first performed at a commercial laboratory in Altha, Fla. by tissue culture in April of 2007. Subsequent propagation by tissue culture has shown that the unique features of this cultivar are stable and reproduced true to type.

SUMMARY OF THE INVENTION

The cultivar 'S39' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'S39.' These characteristics in combination distinguish 'S39' as a new and distinct *Spathiphyllum* cultivar:

1. Very dark green, broad foliage.
2. Early production of secondary foliage, resulting in a full plant growth earlier.
3. Rapidly growing and compact growth habit.

4. Maintains very dark green color under higher than normal light conditions, or low nutrient levels.
5. Spathe production in response to Gibberellic Acid treatment after 10 weeks.
6. Plant habit suitable for 6 inch commercial pots.

PARENT COMPARISON

Plants of the new cultivar 'S39' are similar to the seed parent in most horticultural characteristics. The new variety, however, produces shorter, more compact plants. Additionally, 'S39' produces shorter, narrower leaf blades and shorter petioles than the seed parent. Spathes of 'S39' are smaller and closer to the foliage than the spathes of the seed parent. 'S39' has also shown better resistance to the diseases *Myrothecium* and leaf *Phytophthora* than the seed parent.

Plants of the new cultivar 'S39' are similar to the pollen parent 'Power Petite' U.S. Plant Pat. No. 15,649 in most horticultural characteristics. Plants of the new variety however are more vigorous and faster growing than 'Power Petite'. Additionally, 'S39' produces more leaves and produces additional foliage earlier than 'Power Petite'. Plants of 'S39' are taller than plants of 'Power Petite'. Foliage of the two varieties differs, 'S39' produces darker, more upright foliage with less undulation on the leaf blade than 'Power Petite'. Additionally, plants of 'S39' produce spathes earlier and more abundantly than 'Power Petite'. Plants of 'S39' respond after 10 weeks to the normal GA treatment given to commercial *Spathiphyllum* plants, whereas 'Power Petite' responds after 14 weeks.

COMMERCIAL COMPARISON

'S39' can be compared to compared to the commercial variety *Spathiphyllum* 'S9' U.S. Plant Pat. No. 9,901 Plants of 'S9' are similar to plants of 'S39' in most horticultural characteristics, however, plants of 'S39' are larger and faster growing than 'S9'. 'S39' has much darker, glossier leaves than 'S9.' Additionally 'S39' produces more shoots and has a less undulating leaf margin than 'S9'. Spathes on plants of 'S39' are closer to the foliage than the spathes produced on plants of 'S9'.

'S39' can be compared to compared to the commercial variety *Spathiphyllum* '54905' U.S. Plant. Pat. No. 13,718. Plants of '54905' are similar to plants of 'S39' in most horticultural characteristics, however, plants of 'S39' are shorter than plants of '54905'. 'S39' has much darker, glossier leaves, that are shorter in length than foliage of '54905.' Additionally 'S39' produces foliage with an upright orientation, whereas foliage of '54905' is outwardly arched, creating a more open plant form. Spathes on plants of 'S39' are closer to the foliage than the spathes produced on plants of '54905' Spathes of 'S39' are more elongated compared to the rounder spathe shape of '54905'.

TABLE

| Variety | Serial Number Co-pending | Plant Height | Spathe width |
|---|---|---|---|
| 'S39' | 13/200,513 | 30 cm to top of foliar plane. 58 cm to top of spathe. | 6 cm |
| 'S40' | 13/200,514 | 35 cm to top of foliar plane. 65 cm to top of spathe. | 4.5 to 5.0 cm |
| 'S41' | 13/200,515 | 55 cm to top of foliar plant. 80 cm to top of spathe. | 6 to 8 cm |
| 'S42' | 13/200,509 | 45 cm to top of foliar plant. 65 cm to top of spathe. | 4 to 6 cm |
| 'S43' | 13/200,510 | 60 cm to top of foliar plant. 80 cm to top of spathe. | 5 to 7 cm |

| Variety | Spathe Length | Mature Spathe Color | Quantity of Leaves |
|---|---|---|---|
| 'S39' | 10-12 cm | Front: White 155C Back: White 155C | 70 to 90 in an average of 6 clumps |
| 'S40' | 9 to 12 cm | Front: Green-White 157C Back: Green-White 157C, veins and flush near veins Green 143C | 50 to 60 in an average of 4 to 5 clumps |
| 'S41' | 14 to 16 cm | Front: White 155C Back: White 155C mid vein near Green 143A | 40 to 65 in an average of 8 clumps. |
| 'S42' | 10 to 14 cm | Front: White 155C, but more clear white. Back: White 155C, but more clear white mid vein near Green 143A | 100 to 180 in an average of 12 to 15 clumps. |
| 'S43' | 12 to 14 cm | Front: White 155C, but more clear white. Back: White 155C, but more clear white mid vein near Green 143A | 60 to 100 in an average of 8 to 10 clumps. |

BRIEF DESCRIPTION OF THE PHOTOGRAPH

The accompanying photograph in FIG. 1 illustrates in full color a typical plant of 'S39' grown in a greenhouse in Altha, Fla.

This plant is approximately 9 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'S39' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Plants were treated with Giberellic Acid at 200 ppm, to induce spathe production in approximately 10 weeks. Plants were grown in 80% shade, resulting in approximately 800 to 1200 foot candles of light. Measurements and numerical values represent averages of typical plant types.

Botanical classification: *Spathiphyllum* hybrid 'S39'.

PROPAGATION

Time to initiate roots: Approximately 18 days at approximately 25° C. soil temperature.

Time to produce a fully rooted plantlet: Approximately 14 weeks at approximately 20 to 30° C. soil temperature.

Root description: Thick, fleshy roots with fine, fibrous lateral roots. Color near Orange-White 158D.

PLANT

Growth habit: Rapid, upright.

Plant shape: Upright, leaves only slightly arching out.

Height: Approximately 30 cm to top of foliar plane. Approximately 58 cm to top of tallest spathe.

Plant spread: Approximately 78 cm in a 6 inch pot.

Pot size of plant described: 6 inch.

Growth rate: Moderate.

Branching characteristics: No true branching. Leaves emerge direct from base of plant.

Number of clumps of leaves: 6.

Number of leaves per clump: Average 12.

Number of leaves per plant: Approximately 70 to 90.

Age of plant described: Approximately 9 months.

FOLIAGE

Leaf:

*Arrangement*.—Single leaves emerging basally.

*Average length*(*excluding petiole*).—Approximately 25 cm.

*Average width*.—Approximately 11 cm.

*Shape of blade*.—Elliptic.

*Aspect*.—Slightly undulating and recurved.

*Apex*.—Moderately cirrose.

*Base*.—Attenuate.

*Margin*.—Entire.

*Appearance*.—Glossy.

*Texture of top surface*.—Smooth, glossy.

*Texture of bottom surface*.—Smooth, glossy.

*Color*.—Young foliage upper side: Near Green139A. Young foliage under side: Near Green 137B. Mature foliage upper side: Near Green139A, but darker. Mature foliage under side: Near Green N 138B.

Venation:

*Type*.—Pinnate.

*Venation coloration upper side*.—Near Green 139A.

*Venation coloration under side*.—Near Yellow-Green 144B.

Petiole:

*Length*.—Approximate range between 14 and 22 cm.

*Width*.—At geniculum: Approximately 0.6 cm. Above clump: Approximately 0.9 cm.

*Color*.—Near RHS Green 137A.

*Strength*.—Very strong.

*Other*.—Petiole wing present.

Geniculum:

*Length*.—Approximately 2.5 cm.

*Width*.—Approximately 0.7 cm.

*Color*.—Near RHS Yellow-Green 144B.

Petiole wing/petiole sheath:

*Length*.—Approximately same length as individual petiole, becoming approximately 1 cm longer with age.

*Width*.—Approximately 0.6 cm.

*Color*.—Near RHS Green 137A.

INFLORESCENCE

*Arrangement*.—Spathes with spadices held above the foliage on erect peduncles arising from the petiole sheath.

*Flowering habit*.—Continuous.

*Quantity of spathes per plant*.—On average 4 fully open spathes in good condition.

*Natural flowering season*.—Autumn to Winter.

*Time to flowering*.—10 weeks after standard Gibberellic acid treatment of 200 ppm.

*Fragrance*.—None.

*Self-cleaning or persistent*.—Persistent.

*Flower longevity*.—Flowers stay in good condition approximately 5 weeks on the plant.

Spathe:

*Aspect*.—Cupped.

*Length*.—Approximately 10 to 12 cm.

*Width*.—Approximately 6 cm.

*Shape*.—Elliptic.

*Margin*.—Entire.

*Apex*.—Cirrose.

*Base*.—Cuneate, non-symmetrical.

*Color*.—Front when opening: Near RHS White 155C. Back when opening: Near RHS White 155C. Front when mature: Near RHS White 155C. Back when mature: Near RHS White 155C.

*Fading to*.—Near RHS Green-White 157A.

Spadix:

*Shape*.—Columnar, arising from the top of the peduncle.

*Tip*.—Obtuse.

*Base*.—Obtuse.

*Length*.—Approximately 5.5 cm.

*Width*.—Approximately 1.8 cm.

*Color*.—When opening: Near RHS White 155C. Mature: Near RHS White 155A.

*Quantity of flowers per spadix*.—Approximately 150.

*Spadix flower arrangement*.—Bisexual, rounded.

*Spadix flower diameter*.—Approximately 0.2 cm.

*Spadix flower depth*.—Approximately 0.3 cm.

Peduncle:

*Length*.—Approximately 27 cm, measured from base, which emerges from leaf axil.

*Width*.—Approximately 0.6 cm.

*Color*.—Near RHS Green 141B.

*Strength*.—Very strong.

REPRODUCTIVE ORGANS

All flower parts and reproductive organs are highly reduced, to the point of immeasurable.

*Quantity of pollen*.—Abundant.

*Pollen color*.—Near RHS White 155A.

OTHER CHARACTERISTICS

Disease resistance: Greater resistance than typical of *Spathiphyllum* to *Myrothecium* and leaf *Phytophthora* has been observed.

Drought tolerance and cold tolerance: The new cultivar is a typical *Spathiphyllum*, cold tolerant to approximately 5 to 7° C. and does not tolerate drought.

Fruit/seed production: Not observed.

What is claimed is:

1. A new and distinct cultivar of *Spathiphyllum* plant named 'S39' as herein illustrated and described.

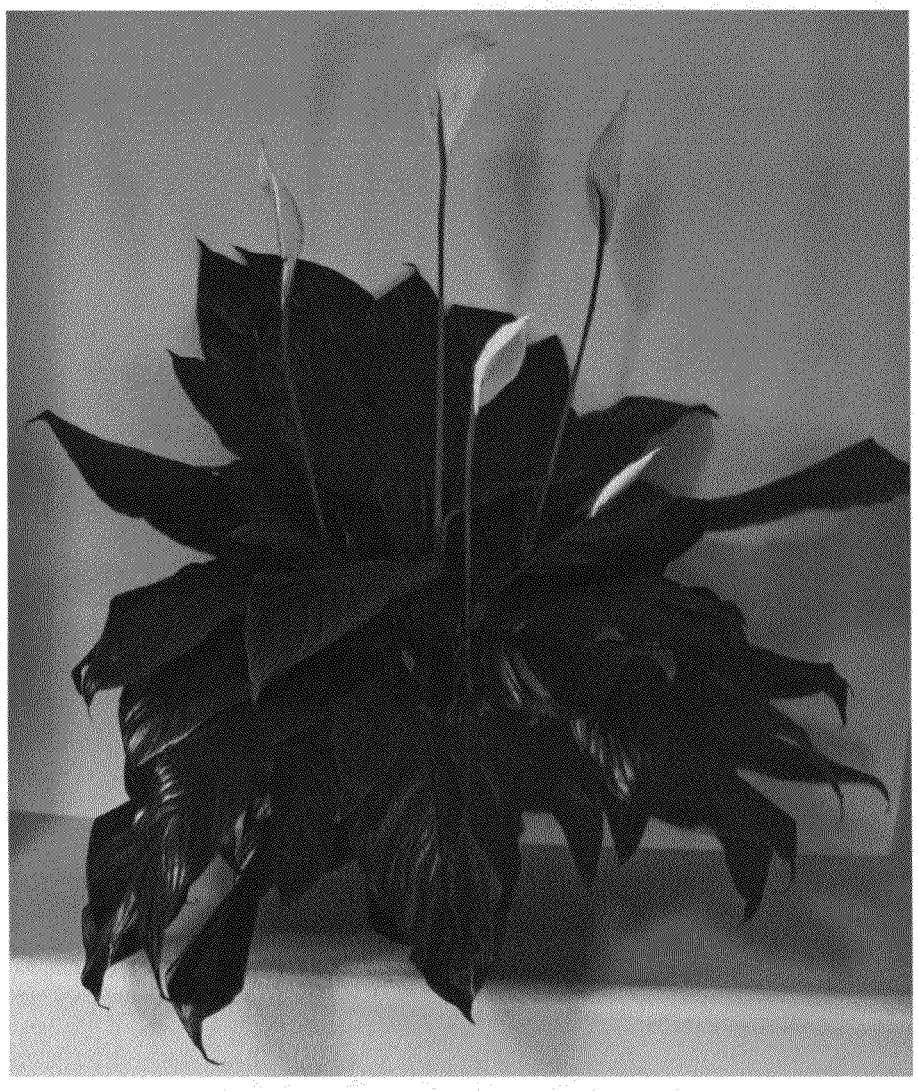

* * * * *